United States Patent [19]

Petree et al.

[11] 4,106,927

[45] Aug. 15, 1978

[54] NON-EXPLOSIVE GLYOXIME COMPOSITIONS

[75] Inventors: Harris E. Petree, Kernersville; James B. Nabors, Jr., Greensboro, both of N.C.; Henry C. Grace, Baton Rouge, La.

[73] Assignee: Ciba-Geigy Corporation, Ardsley, N.Y.

[21] Appl. No.: 709,134

[22] Filed: Jul. 27, 1976

[51] Int. Cl.$^2$ .......................... A01N 9/20; A01N 9/02
[52] U.S. Cl. .................................... 71/121; 71/128
[58] Field of Search .................. 71/121; 260/566 A

[56] References Cited

U.S. PATENT DOCUMENTS

| | | | |
|---|---|---|---|
| 2,121,472 | 6/1938 | Niederl et al. | 260/566 A |
| 2,821,555 | 1/1958 | Doerner | 71/121 |
| 2,883,407 | 4/1959 | Flenner | 260/431 |
| 3,001,908 | 9/1961 | Harrison | 424/283 |
| 3,515,536 | 6/1970 | Hill et al. | 71/121 X |
| 3,869,278 | 3/1975 | Wilcox | 71/121 |

FOREIGN PATENT DOCUMENTS

73/5140   7/1974   South Africa.

OTHER PUBLICATIONS

Weygand/Hilgetog, "Preparative Organic Chemistry," 1972, John Wiley & Sons, p. 513.

*Primary Examiner*—Joseph Paul Brust
*Attorney, Agent, or Firm*—Harry Falber

[57] ABSTRACT

A thermally stable water soluble glyoxime composition comprising a blend of glyoxime and an ethylene glycol-type material and a process for the preparation thereof comprising reacting glyoxal and a hydroxylamine acid salt in the presence of said ethylene glycol-type material.

21 Claims, No Drawings

NON-EXPLOSIVE GLYOXIME COMPOSITIONS

Glyoxime may be readily synthesized by the reaction of glyoxal and a hydroxylamine acid salt according to the following reaction mechanism illustrated in terms of the sulfate salt

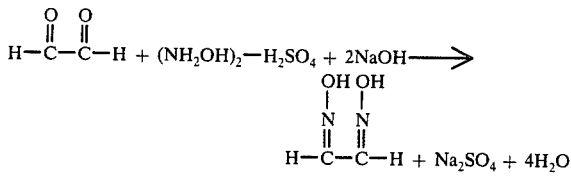

The acid salts may be derived from a variety of inorganic or organic acids and may comprise sulfates, chlorides, acetates, carbonates, oxalates, and the like. Correspondingly, the hydroxylamine salt may be replaced by an appropriate oxime, such as acetone oxime, wherein the precursor aldehyde or ketone has a boiling point below that of the resulting oxime.

The dry glyoxime product has, however, been rated moderately shock sensitive, the energy released upon detonation being slightly higher than that released by TNT. Sustained temperatures above 100° C can also result in detonation if the product is confined and in deflagration if the product is in a vented container. The apparent cause for these characteristics is an autocatalytic reaction initiated subsequent to an induction period. Clearly, these conditions cause havoc with the formulation of glyoxime for its various known applications, such as a reagent for various colorimetric and gravimetric procedures. Thus, grinding must be avoided due to the shock potential. Fire hazard, dust explosion and flammable gas emission must be considered. Drying must be conducted at low temperatures under vacuum and in equipment which will not subject the material to frictional or shock forces. Glyoxime isolation as a dry solid has the potential for being extremely hazardous.

Accordingly, it is the object of this invention to provide a non-explosive formulation for glyoxime.

It is a further object of this invention to provide a process for preparing and formulating glyoxime which substantially eliminates the hazards of shock and excessive heat.

It is still a further object to provide a formulation which is compatible with the various uses for glyoxime and which, in fact, increases the biological activity of glyoxime.

Various other objects and advantages of this invention will become apparent from the following description thereof.

It has now been discovered that glyoxime formulations can be prepared which are not susceptible to the hazards of shock and excessive heat. Thus, such formulations release substantially reduced amounts of exothermic heat and provide a low thermal output on decomposition. Furthermore, they are prepared by processes either which do not require isolation of the glyoxime as a dry solid for subsequent formulation, thereby avoiding the hazards encountered with the dried product, or which do prepare dry material but are adapted so as to minimize the potential hazard.

These novel formulations may be in solution form or in soluble, powder form. In either instance, the key additional element in the formulation is an ethylene glycol type material such, for example, as liquid ethylene glycols, liquid polyethylene glycols and polyethylene glycol monomethylethers, solid polyethylene glycols, and polyglycols derived from the chain growth of ethylene glycol on various mono- or poly- alcohols. These glycols provide significant reductions of exotherm, with the resulting formulations exhibiting low thermal output on decomposition. Accordingly, the shock and thermal sensitivity of such typical glyoxime products are substantially minimized. It is to be noted that many of the glycols provide reduction of exotherm far beyond the simple dilution effect anticipated as a result of the presence of glycol. They also generally exhibit low volatility so as to provide long term stabilization.

The processes of this invention developed for the preparation and formulation of glyoxime generally avoid the step of isolating glyoxime as a dry product. Rather, one approach involves reacting glyoxal and hydroxylamine salt in the presence of the glycol solvent such that a stable, completely formulated product is obtained. A second approach is to conduct the reaction in an aqueous medium and then dissolve the resulting slightly dried glyoxime paste in a desired glycol solvent to the desired concentration. A third approach relating to the preparation of soluble, powder formulations involves either dissolving the glyoxime wet cake in the desired liquid glycol solvent or molten solid glycol solvent and then drying the formulation, or merely blending dry solids as by adding the glyoxime to the solid glycol component. While these latter procedures are not preferred, they are nevertheless feasible due to the absence of process steps which encourage shock sensitivity.

Among the several uses for glyoxime, South African Pat. No. 73/5140, issued July, 3, 1974, discloses its use for fruit abscission, i.e. the ability to facilitate the harvesting of fruits by assisting in the loosening thereof. It has now been determined that the presence of the glycol component in the novel glyoxime formulations of this invention exerts a significant effect on this biological activity of glyoxime. Thus, not only is there produced a stable formulation with retention of performance characteristics, but one with significantly increased biological activity.

Regardless of the physical form of the resulting formulation, the water-soluble ethylene glycol component utilizable therein includes glycols such as ethylene glycol, diethylene glycol, triethylene glycol and tetraethylene glycol; liquid polyethylene glycols ranging in average molecular weight from about 200 to 600; solid polyethylene glycols ranging in average molecular weight from about 1000 to 7500; ethylene and polyethylene glycol monomethyl ethers such as 2-methoxyethanol, 2-(2-methoxyethoxy)ethanol, 1-methyl-2-methoxyethanol and 1-methyl-2-(1-methyl-2-methoxyethoxy)ethanol; the chain growth glycols noted hereinabove; and mixtures thereof. Such polyethylene glycols are commercially sold by Union Carbide Corporation under the trademark designation of CARBOWAX. The glycol ethers are also commercially sold by Union Carbide Corporation under the trademark designations CELLOSOLVE, CARBITOL and UCAR. The chain growth glycols are sold commercially by the Jefferson Chemical Corporation. The preferred glycol components are the liquid polyethylene glycols having an average molecular weight in the range of from about 300 to 600.

As previously noted, the formulations of this invention may be prepared in several ways depending upon the final physical form of the formulation. The preferred process for the preparation of liquid formulations can be characterized as an in-situ process, i.e. the glycol component is utilized as the medium for the glyoxime reaction. Thus, glyoxal is charged into a reaction medium comprising a hydroxylamine salt, the glycol component and water and the reaction is allowed to proceed while the exothermic temperature is maintained at from about 20°-40° C. It is to be noted that up to about 50%, by weight, of extraneous water, i.e. water not present in the reactants, may be added to the glycol reaction medium. The reaction generally continues for a period of about 30-60 minutes in order to insure total glyoxal reaction, whereupon the pH level of the system is adjusted to from about 4 to 6 by the addition of a base such as alkali and alkaline-earth metal hydroxides, bicarbonates, and the like. Basic pH levels are to be avoided in view of the resulting poor stability of the glyoxime formulation. At this point, and in view of the necessary addition of base, separation occurs between the aqueous phase containing the acid salt and the glycol phase containing the dissolved glyoxime product. Separation of the phases and water removal from the glycol layer produces a formulation of glyoxime in glycol. The concentration of glyoxime may then be adjusted to a desired level, although the glyoxime concentration will not exceed about 20%, by weight, due to solubility considerations. Substantially quantitative yields of glyoxime as the single reaction product are obtained.

An alternative approach for preparing liquid formulations involves reacting the glyoxal and the hydroxylamine salt in an aqueous medium. Temperatures of reaction and pH adjustments are substantially identical to those described in the in-situ process. Filtration and washing with minimum amounts of water to avoid product loss yield a glyoxime paste product. Water is then removed to provide a paste product generally having a solids content of from about 50 to 80%, by weight, although these figures may vary. The paste is subsequently dissolved in a glycol component to the desired glyoxime concentration (maximum of about 20%, by weight) and water is removed to yield the glyoxime formulation. It is to be noted that up to about 5%, by weight, of water, and preferably 3%, may be retained in the resulting formulation without encountering possible corrosion considerations.

With regard to reactant concentrations in either process, the glyoxal and hydroxylamine salt are present in molar ratios ranging from a stoichiometric relationship to about a 10% molar excess of hydroxylamine salt, and preferably up to about a 5% molar excess, the excess facilitating total reaction of the glyoxal.

Optional ingredients may, if desired, be added during the solubilization of the paste in the glycol solvent. Borate esters such as methyl cellosolve borate, 2-ethylhexanol borate, and the like, may be added in concentrations ranging from about 5 to 25%, by weight, to further reduce the exothermic heat potential.

Regardless of the process utilized to prepare these liquid formulations, the result is elimination of dry, solid glyoxime isolation and the potential instability and explosiveness associated therewith. Rather, a stable, solvent formulated material ready for immediate use is prepared.

The processes for preparing solid formulations utilizing solid ingredients without increasing the risk of instability involve (1) blending the dry solids as by adding glyoxime to a solid glycol component; or (2) melting a blend of the dry solids at a temperature below about 65° C. to avoid thermal instability, removing any water content, cooling and flaking by the use of conventional equipment. Glyoxime concentrations ranging up to about 50%, by weight, may be achieved in the solid formulations.

The glyoxime-glycol formulations are not phytotoxic in the usual application concentrations, and they have low toxicity towards warm-blooded animals. They moreover produce no morphological changes of the plants or cause damage to them. They promote, in particular, the development of abscission layers, particularly between stalks and petioles. Consequently, fruits of all kinds, e.g. stone fruit (cherries), berries, grape vines, pomaceous fruit (apples) or oil fruits (olives), and particularly citrus fruits such as oranges, lemons, grapefruit, etc., can be separated from the fruit stems, manually or mechanically, without any great amount of force being applied. Damage to foliage and branches which normally occurs when fruit is removed by the shaking of trees and shrubs, or by the plucking of the fruit from the branches, is largely avoided, and the production capacity of the trees thus increased.

The extent and nature of the action are governed by the most diverse factors, depending on the type of plant, particularly, however, on the applied concentration and on the time of application with regard to the stage of development of the plant and the fruit. Thus, for example, plants of which the fruit is to be sold, or in some other way utilized, are treated immediately after blossoming or at an appropriate length of time before the gathering of the fruit, i.e. 3 days to 4 weeks. The active substances are applied in the form of liquid preparations, these being applied to parts of plants above the soil, to the surface of the soil or into the soil. Application to parts of plants above the soil is preferred, for which purpose solutions or aqueous dispersions are most suitable.

The applied amounts are largely governed by the purpose and nature of the application (treatment of the soil or of parts of plants). The usual amounts applied in the case of soil treatment and for crops are between 0.1 and 16 kg. and preferably 1 to 4 kg., of active substance per hectare of land under cultivation.

The unanticipated benefit provided by the instant glyoxime-glycol formulations is the synergistic effect exerted by the glycol component on the biological activity of glyoxime, i.e. the activity of formulated glyoxime exceeds the sum total of the activity exhibited by glyoxime and glycol individually. Thus, it was determined that, in many instances, the activity of glyoxime in these formulations substantially exceeds that of a water solution of glyoxime, as determined on the basis of equivalent active ingredient concentrations. It is therefore seen that the instant processes and formulations provide both a mechanism for eliminating the hazards of shock and excessive heat conventionally encountered with glyoxime and a mechanism for significantly increasing the biological activity of glyoxime.

The following examples further illustrate the embodiment of this invention. All parts given in these examples are by weight unless otherwise noted.

EXAMPLE I

This example illustrates the preparation of glyoxime by means of the preferred procedure of this invention.

A reaction vessel containing aqueous polyethylene glycol (Carbowax 400) and hydroxylamine sulfate (1.02 moles) was charged with 40%, by weight, aqueous glyoxal (1.0 mole). The temperature of the resulting exothermic condensation reaction ranged from about 25°–40° C. Thereafter, the reaction system was adjusted to a pH level of 4.5 by the addition of 50%, by weight, aqueous sodium hydroxide solution. Thereafter, a two phase system resulted whereby a saturated salt solution formed as the lower aqueous, product-free layer and a polyethylene glycol, glyoxime product solution substantially free of water formed as the upper layer. The lower layer was removed and the product layer was stripped free of water. The glyoxime product concentration was then adjusted to 10%, by weight, producing a readily utilizeable glyoxime formulation. A near quantitative yield of glyoxime was obtained.

EXAMPLE II

This example provides an alternative method for the preparation of glyoxime.

A reaction vessel was charged with 90 grams water and 145.1 grams (1.00 mole) 40% aqueous glyoxal. Under agitation, 169.2 grams of 97% hydroxylamine sulfate (1 mole) was charged, whereby the temperature dropped to 10° C. Under agitation, addition of 50%, by weight, aqueous sodium hydroxide solution (2.025 moles) was initiated. During the first half of the sodium hydroxide addition the temperature of the solution rose slowly to about 35° C. External cooling was then applied to control the reaction temperature below 40° C. The sodium hydroxide addition required 33 minutes, and the final solution pH was 4.6. The reaction mass was held at 35° C for approximately 2 hours, then the slurry was vacuum filtered. The slurry was washed with water at 35° C to remove sodium sulfate present. The wet cake obtained weighed 123.8 grams and had a solids content of 68.4%. The yield of glyoxime was 93.6%.

Formulation of this material can be achieved by blending the wet cake with polyethylene glycol (Carbowax 400) and removing water by vacuum distillation. By this procedure a readily utilizable 10%, by weight, glyoxime solution can be prepared.

EXAMPLE III

The following formulations were prepared utilizing the procedure set forth in Example I, hereinabove.

| | parts, by weight | | | | | | | |
|---|---|---|---|---|---|---|---|---|
| | 3 | 4 | 5 | 6 | 7 | 8 | 9 | 10 |
| Glyoxime | 10 | 10 | 10 | 10 | 15 | 15 | 10 | 10 |
| Polyethylene Glycol 200 | 90 | — | — | — | — | — | — | — |
| Polyethylene Glycol 300 | — | 90 | — | — | — | — | — | — |
| Polyethylene Glycol 350 | — | — | 90 | — | — | — | — | — |
| Polyethylene Glycol 550 | — | — | — | 45 | — | — | — | — |
| 2-methoxyethanol | — | — | — | 45 | 85 | — | — | — |
| 2-(2-methoxyethoxy)ethanol | — | — | — | — | — | 85 | — | — |
| 1-methyl-2-methoxyethanol | — | — | — | — | — | — | 90 | — |
| 1-methyl-2-(1-methyl-2-methoxyethoxy)ethanol | — | — | — | — | — | — | — | 90 |

EXAMPLE IV

The following formulations were prepared according to the procedure set forth in Example II, hereinabove. Optional ingredients were added during the solubilization of the glyoxime paste.

| | parts, by weight | | | | | | | | | | | | | |
|---|---|---|---|---|---|---|---|---|---|---|---|---|---|---|
| | 11 | 12 | 13 | 14 | 15 | 16 | 17 | 18 | 19 | 20 | 21 | 22 | 23 | 24 |
| Glyoxime | 10 | 10 | 10 | 10 | 10 | 10 | 10 | 15 | 15 | 10 | 10 | 10 | 10 | 10 |
| Polyethylene glycol 400 | 85 | 80 | 65 | — | — | — | — | — | — | — | — | — | — | 87.5 |
| Polyethylene glycol 350 | — | — | — | 85 | 80 | — | — | — | — | — | — | — | — | — |
| 1-methyl-2-(1-methyl-2-methoxyethoxy)ethanol | — | — | — | — | — | 85 | 80 | — | — | — | — | — | — | — |
| 2-(2-methoxyethoxy)ethanol | — | — | — | — | — | — | — | 80 | 75 | — | — | — | — | — |
| 1-methyl-2-methoxyethanol | — | — | — | — | — | — | — | — | — | 85 | 80 | — | — | — |
| 2-methoxyethanol | — | — | — | — | — | — | — | — | — | — | — | 80 | 65 | — |
| Methylcellosolve borate | 5 | 10 | 25 | 5 | 10 | 5 | 10 | 5 | 10 | 5 | 10 | — | — | — |
| 2-ethylhexanol borate | — | — | — | — | — | — | — | — | — | — | — | 10 | 25 | — |
| Water | — | — | — | — | — | — | — | — | — | — | — | — | — | 2.5 |

EXAMPLE V

In order to determine the thermal stability of the novel formulations of this invention, the formulations noted hereinbelow were subjected to a differential scanning calorimetry procedure. The tests were conducted with a Perkin-Elmer Differential Scanning Calorimeter-1B at a scanning rate of 10° C/minute. The samples were tested in sealed cups.

| | DSC Data from Sample Exotherm (Dynamic Scan 10° C/min) | | |
|---|---|---|---|
| Formulation # | Exotherm Range (° C) | Peak (° C) | Average ΔH (cal/gram) |
| Glyoxime, Tech (93.1%) | 190–223 | 210 | 708 |
| 1 | 212–308 | 257 | 64 (33)* |
| 11 | 210–275 | 230 | (31)* |
| 12 | 200–285 | 236 | (29)* |
| 13 | 237–262 | 252 | 18 |
| 5 | 205–287 | 265 | 64 |
| 14 | 245–305 | 270 | 37 |
| 15 | 237–300 | 265 | 37 |
| 10 | 250–255 | 252 | 1 |
| 16 | 255–270 | 260 | 1 |
| 17 | 255–275 | 260 | *open 1 |
| 8 | 218–222 | 220 | 1 |
| 18 | 230–240 | 235 | 1 |
| 19 | 247–260 | 253 | 1.5 |
| 9 | 220–247 | 237 | 28 |
| 20 | 225–240 | 235 | 23 |
| 21 | 225–250 | 237 | 22 |
| 7 | 195–250 | 228 | 110 |
| 22 | 215–230 | 220 | 15 |
| 23 | 225–244 | 231 | 5.5 |
| 24 | 213–308 | 256 | 60 |

*open cup measurement

The data presented hereinabove clearly illustrates the substantially improved thermal stability of the formulations of this invention, particularly as noted by the high temperature of initiation of exotherm and the substantially reduced thermal output on decomposition.

EXAMPLE VI

The following soluble solid formulations were prepared by means of a procedure which involved blending the dry ingredients by mixing the glyoxime and the boric acid into the polyethylene glycol.

| | parts, by weight | |
|---|---|---|
| | 26 | 27 |
| Glyoxime | 33.4 | 33 |
| Polyethylene glycol 6000 | 33.3 | 42 |
| Boric Acid | 33.3 | 25 |

These formulations exhibited no evidence of exothermic behavior in DSC scans (see Example V) over a range of 55°–250° C at a scanning rate of 10° C/minute. They also showed no evidence of shock sensitivity utilizing a 5 kilogram drophammer apparatus.

EXAMPLE VII

This example illustrates the improved fruit abscission utility of the novel formulations of this invention.

A. Branches of hamlin orange trees were sprayed with aqueous solutions of the active-substance formulations at the indicated concentrations shortly before harvesting. The evaluation of the test results was made after four days on two replicates by determining the number of shed oranges compared with the control specimens (% fruit drop), the rating from 0–100 indicating the degree of rind burn exhibited by the oranges (fruit injury), the latter being indicative of increased activity, and the amount of undesirable foliage drop (% leaf drop). The results of these tests are noted in the following table.

| Formulation No. | Application Rate (ppm) | % Fruit Drop | Fruit Injury | % Leaf Drop |
|---|---|---|---|---|
| Glyoxime Tech. | 250 | 2.5 | 20.0 | 0.0 |
| | 500 | 10.0 | 32.5 | 0.0 |
| 9 | 250 | 2.5 | 25.0 | 0.0 |
| | 500 | 10.0 | 47.5 | 0.0 |
| 10 | 250 | 0.0 | 25.0 | 0.0 |
| | 500 | 22.5 | 47.5 | 0.0 |
| 11 | 250 | 5.0 | 40.0 | 0.0 |
| | 500 | 72.5 | 80.0 | 2.5 |
| 12 | 250 | 52.5 | 80.0 | 2.5 |
| | 500 | 82.5 | 92.5 | 5.0 |
| 13 | 250 | 12.5 | 45.0 | 0.0 |
| | 500 | 32.5 | 52.5 | 0.0 |
| 22 | 250 | 2.5 | 27.5 | 0.0 |
| | 500 | 5.0 | 32.5 | 0.0 |
| 23 | 250 | 10.0 | 42.5 | 0.0 |
| | 500 | 37.5 | 70.0 | 0.0 |

B. The procedure described in (A) hereinabove was repeated with the exceptions that the solutions were sprayed onto whole hamlin orange tree specimens and evaluation took place six days after application.

| Formulation No. | Application Rate (ppm) | % Fruit Drop | Fruit Injury | % Leaf Drop |
|---|---|---|---|---|
| Control | — | 0.0 | 0.0 | 0.0 |
| Glyoxime Tech. | 375 | 13.3 | 43.3 | 0.0 |
| 1 | 375 | 63.3 | 56.7 | 1.7 |
| 5 | 375 | 45.0 | 45.0 | 2.5 |
| 9 | 375 | 23.3 | 43.3 | 1.7 |
| 10 | 375 | 28.3 | 33.3 | 0.0 |
| 11 | 375 | 56.7 | 63.3 | 1.7 |
| 12 | 375 | 63.3 | 70.0 | 3.3 |
| 14 | 375 | 70.0 | 73.3 | 5.0 |
| 15 | 375 | 55.0 | 66.7 | 5.0 |
| 19 | 375 | 26.7 | 50.0 | 1.7 |

-continued

The results presented hereinabove clearly illustrate the generally significantly improved fruit abscission activity of the novel formulations of this invention in contrast to water solutions of glyoxime. Furthermore, since it is anticipated that the previously defined ethylene glycol-based components will exhibit no abscission activity, these results also clearly illustrate the synergistic effect exerted by the glycol component on the biological activity of glyoxime and, correspondingly, the synergism of the resulting formulations.

Summarizing, it is seen that this invention provides novel non-explosive glyoxime compositions as well as an in-situ process for the preparation thereof. Variations may be made in materials, procedures and proportions without departing from the scope of the invention as defined by the following claims.

What is claimed is:

1. A composition for facilitating the harvesting of fruit and having thermal and shock stability which comprises a blend of glyoxime and at least one water soluble ethylene glycol-based component selected from the group consisting of liquid polyethylene glycols having an average molecular weight of from about 200 to 600, and solid polyethylene glycols having an average molecular weight of from about 1000 to 7500.

2. The composition of claim 1, which is in liquid form and wherein said glyoxime is present in a maximum concentration of about 20%, by weight.

3. The composition of claim 2, wherein said ethylene glycol-based component is selected from liquid polyethylene glycols having an average molecular weight of from about 300 to 600.

4. The composition of claim 2 which also contains up to about 5%, by weight, of water.

5. The composition of claim 2 which also contains from about 5 to 25%, by weight, of a soluble borate ester.

6. The composition of claim 1 which is in solid form and wherein said glyoxime is present in a maximum concentration of about 50%, by weight.

7. The composition of claim 6, wherein said ethylene glycol-based component is selected from solid polyethylene glycols having an average molecular weight of from about 1000 to 7500.

8. The composition of claim 6 which also contains boric acid.

9. A process for the preparation of a glyoxime composition useful for facilitating the harvesting of fruit and having thermal and shock stability which comprises the steps of reacting glyoxal with a hydroxylamine acid salt in the presence of at least one liquid, water soluble ethylene glycol-based component, adjusting the pH of the system to a level of from about 4–6, and isolating a solution of glyoxime in said ethylene glycol-based component.

10. The process of claim 9, wherein said reaction is conducted at a temperature of from about 20°–40° C.

11. The process of claim 9, wherein said glyoxal is charged into a blend of said ethylene glycol-based component and said hydroxylamine acid salt.

12. The process of claim 9, wherein said glyoxal and said hydroxylamine acid salt are present in a concentration ranging from stoichiometric amounts to about a 10% molar excess of said acid salt.

13. The process of claim 9, wherein said ethylene glycol-based component is selected from the group consisting of liquid polyethylene glycols having an average molecular weight of from about 200 to 600.

14. The process of claim 13, wherein said ethylene glycol-based component is selected from liquid polyethylene glycols having an average molecular weight of from about 300 to 600.

15. A process for reducing the thermal and shock instability of glyoxime having usefulness for facilitating the harvesting of fruit which comprises blending of said glyoxime with at least one water soluble ethylene glycol-based component selected from the group consisting of liquid polyethylene glycols having an average molecular weight of from about 200 to 600, solid polyethylene glycols having an average molecular weight of from about 1000 to 7500.

16. The process of claim 15, wherein a liquid composition is formed and said glyoxime is present in a maximum concentration of about 20%, by weight.

17. The process of claim 16, wherein said ethylene glycol-based component is selected from liquid polyethylene glycols having an average molecular weight of from about 300 to 600.

18. The process of claim 16, wherein said glyoxime is in the form of an aqueous paste containing from about 50-80%, by weight, of water and, subsequent to said blending, said water is removed such that no more than about 5%, by weight, thereof is retained in the resulting composition.

19. The process of claim 16, wherein from about 5-25%, by weight, of a soluble borate ester is also added to said liquid composition.

20. The process of claim 15, wherein a solid composition is formed and said glyoxime is present in a maximum concentration of about 50%, by weight.

21. The process of claim 20, wherein boric acid is also added to said solid composition.

* * * * *